United States Patent
Mandai et al.

(10) Patent No.: US 6,306,893 B1
(45) Date of Patent: *Oct. 23, 2001

(54) TAXOID DERIVATIVES AND PROCESS FOR PRODUCING THE SAME

(75) Inventors: Tadakatsu Mandai, 2-1-19-301, Kitagata, Okayama-shi 700 (JP); Hiroshi Okumoto, Okayama (JP); Koji Hara, Kanagawa (JP); Katsuhiko Mikuni, Kanagawa (JP); Kozo Hara, Kanagawa (JP); Yoshinori Tsuchiya, Tokyo (JP); Kosho Nakamura, Kyoto (JP); Teruhiko Umetsu, Tokyo (JP)

(73) Assignees: Ensuiko Sugar Refining Company, Ltd; Bio Research Corporation of Yokohama; Tadakatsu Mandai; Kaken Pharmaceutical Company, Ltd., all of (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/529,208
(22) PCT Filed: Oct. 27, 1997
(86) PCT No.: PCT/JP97/03615
  § 371 Date: Apr. 7, 2000
  § 102(e) Date: Apr. 7, 2000
(87) PCT Pub. No.: WO99/18113
  PCT Pub. Date: Apr. 15, 1999
(51) Int. Cl.[7] .................. A61K 3/335; C07D 305/00; C07D 407/00
(52) U.S. Cl. ................ 514/449; 549/510; 549/414
(58) Field of Search .................. 549/510; 514/449, 514/414

(56) References Cited

U.S. PATENT DOCUMENTS

| 4,857,653 | 8/1989 | Colin et al. |
| 5,767,297 | * 6/1998 | Mandai et al. ............ 549/510 |

FOREIGN PATENT DOCUMENTS

| 781778 A1 | 7/1997 | (EP) . |
| 9-241293 | 9/1997 | (JP) . |

* cited by examiner

*Primary Examiner*—Deborah C. Lambkin
(74) *Attorney, Agent, or Firm*—Ronald I. Eisenstein

(57) ABSTRACT

An object of the invention is to develop galactose or mannose derivatives of docetaxel, etc. having improved solubility and physiological activity, to alleviate burden imposed on patients and to provide effective therapeutic drug for tumors.

The present invention provides taxoid derivatives comprising any of paclitaxel, docetaxel and 10-deacetyl-baccatin III to which galactose or mannose is linked through a spacer, and methods for producing taxoid derivatives comprising reacting paclitaxel, docetaxel or 10-deacetyl-baccatin III with tetrabenzyl acetyloxygalactoside or tetrabenzyl acetyloxymannoside, subjecting the product to debenzylation reaction, and optionally to detriethylsilylation reaction.

27 Claims, 1 Drawing Sheet

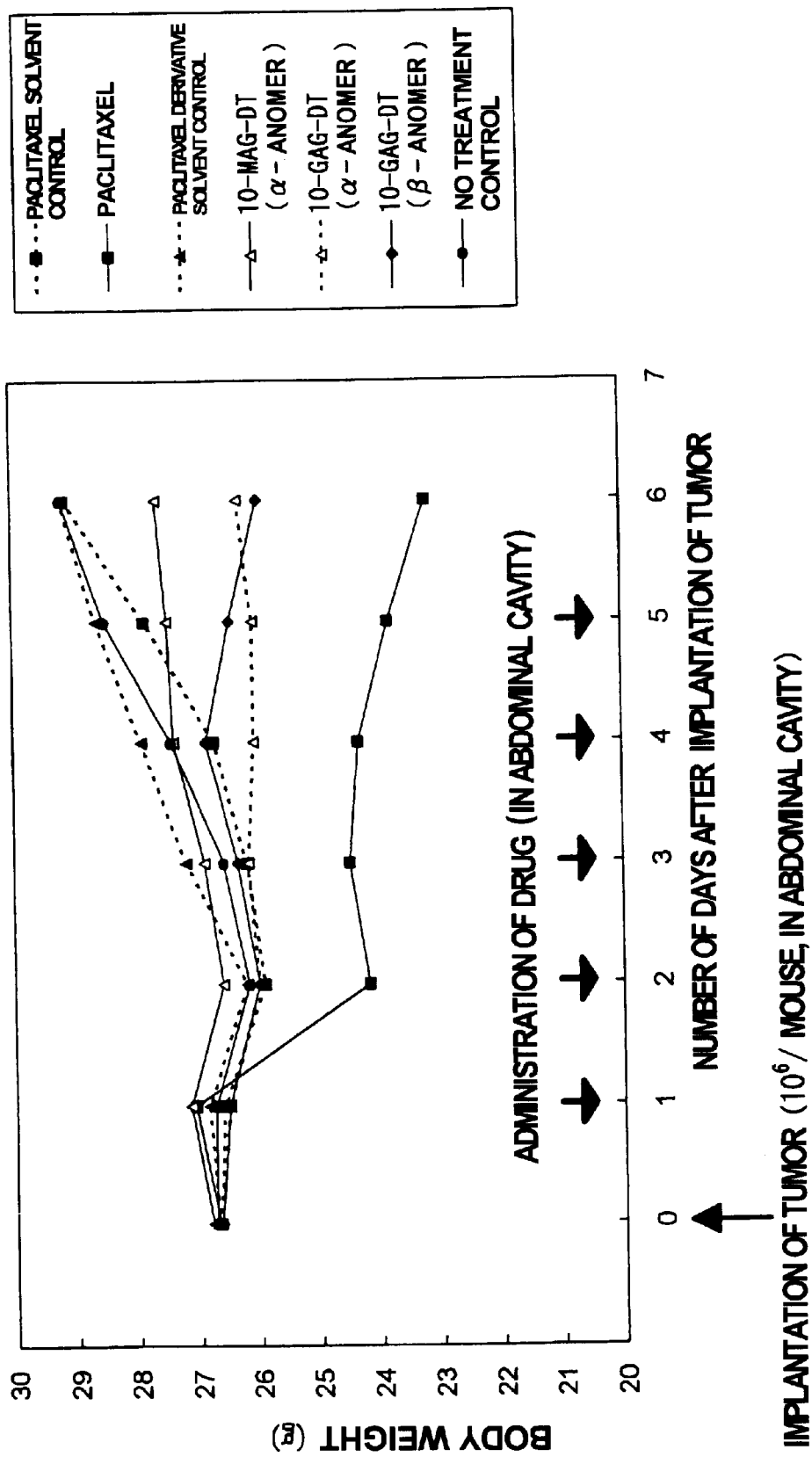

TAXOID DERIVATIVES AND PROCESS FOR PRODUCING THE SAME

This application is a 371 of PCT/JP97/03615 Oct. 27, 1997.

TECHNICAL FIELD

The present invention relates to taxoid derivatives and process for producing the same and more particularly to taxoid derivatives having improved physiological activity and solubility in water by linking galactose or mannose to any one of paclitaxel, docetaxel and 10-deacetyl-baccatin III through a spacer, and process for producing the same.

TECHNICAL BACKGROUND

Paclitaxel is a diterpene compound isolated from the bark of a yew tree of North American growth (Taxus brevifolia) [M. C. Wani et al.: J. Am. Chem. Soc., 93, 2325 (1971)] andis apotent antitumor agent having improving effect against tumors that cannot be cured by conventional chemical therapy. The mechanism by which taxol controls a tumor is specific; it causes excessive formation of a microtubule to inhibit mitosis in contrast to many conventional antitumor agents that inhibit the formation of a microtubule, which is a major component of a spindle, mitotic apparatus.

Although paclitaxel is an important antitumor agent, it is low solubility in water and hence its application as a therapeutic drug is limited. Accordingly, studies on improvement of its solubility by use of a solubilizing agent or converting it into derivatives have been made intensively. However, no satisfactory solution has been found yet. For example, currently paclitaxel is administered together with "Cremophor", a solubilizing agent. This is performed by administering 1 liter over 6 hours every 2 weeks, which is practiced for 4 cycles, and imposes the patient with a heavy burden [Eric K. Rowinsky et al.: CANCER RESEARCH, 49, 4640 (1989)] and in addition has the problem that the solubilizing agent has side effects.

Also, docetaxel has been developed as a paclitaxel derivative having improved solubility. The solubility in water of docetaxel is only 35 times as high as taxol [I. Ringel et al.: J. Natl. Cancer Inst., 83, 288 (1991)], and is not so much improved.

To improve the solubility of paclitaxel, introduction of various functional groups to a side chain or nucleus of taxol has been tried. However, improvement of solubility was observed on some compounds of such derivatives but none has been reported that has increased physiological activity.

No report has been made on sugar derivatives of paclitaxel only one exception is the report on the existence of a compound consisting of paclitaxel and xylose attached thereto naturally through an ether bond [H. Lataste et al.: Proc. Natl. Acad. Sci. USA, 81, 4090 (1984)].

Chemical glycosylation of paclitaxel includes many known methods as described in, for example, "Experimental Chemistry Course 26, Organic Synthesis VIII, Chapter 3, 4th Edition, edited by Japan Chemical Society", any of which methods must use a heavy metal or strong Lewis acid. However, since paclitaxel and docetaxel have an oxetane skeleton, which is unstable to acids, and a basic skeleton having high stereo hindrance, conventional chemical glycosylation process does not proceed efficiently. On the other hand, glycosylation with an enzyme results in failure of obtaining the target compound because of very low solubility in water of paclitaxel and docetaxel.

Furthermore, 10-deacetyl-baccatin III extracted from a yew tree of North American growth (Taxus brevifolia) like paclitaxel is a precursor of docetaxel, so that development of a method for producing hydrophilic taxoid derivatives can be expected by use of this substance.

DISCLOSURE OF THE INVENTION

Under the circumstances, an object of the present invention is to develop derivatives of paclitaxel, etc. having improved solubility and physiological activity and provide an effective therapeutic drug for tumors that imposes less burden on patients.

The present inventors have made intensive research with view to developing derivatives of paclitaxel and as a result found that there can be obtained paclitaxel derivatives that consists of paclitaxel, and galactose or mannose linked thereto via an ester bond through a spacer and that the resulting derivatives show improved solubility in water and physiological activity. The present invention has been accomplished based on this discovery. Also, as for docetaxel and 10-deacetyl-baccatin III described above, the present inventors have established methods for preparing taxoid derivatives in which galactose or mannose is linked via an ester bond in a similar manner.

That is, the present invention relates to taxoid derivatives comprising any one of paclitaxel, docetaxel and 10-deacetyl-baccatin III to which galactose or mannose is linked through a spacer, to methods for producing the same and to their use.

BRIEF DESCRIPTION OF DRAWINGS

FIG. 1 is a graph illustrating effect of taxoid derivatives on the body weight of P388 leukemia cell implanted mouse.

BEST MODE FOR CARRYING OUT THE INVENTION

Hereinafter, the present invention will be explained.

Specific examples of the taxoid derivatives of the present invention will be shown below. In the formulae, Ph shows a phenyl group, Bz shows a benzyl group, and Ac shows an acetyl group, respectively.

Galactosyloxyacetyl-7-paclitaxel (hereinafter, abbreviated as "7-GAG-PT") of the following formula, Mannosyloxyacetyl-7-paclitaxel (hereinafter, abbreviated as "7-MAG-PT") of the following formula,

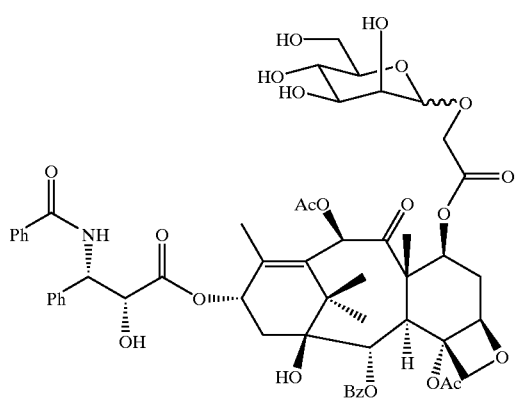

Galactosyloxyacetyl-10-paclitaxel (hereinafter, abbreviated as "10-GAG-PT") of the following formula,

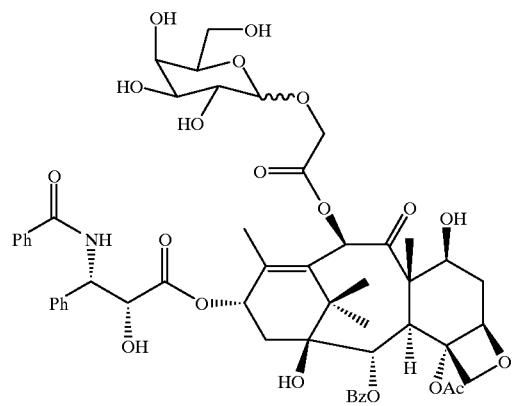

Mannosyloxyacetyl-10-paclitaxel (hereinafter, abbreviated as "10-MAG-PT") of the following formula,

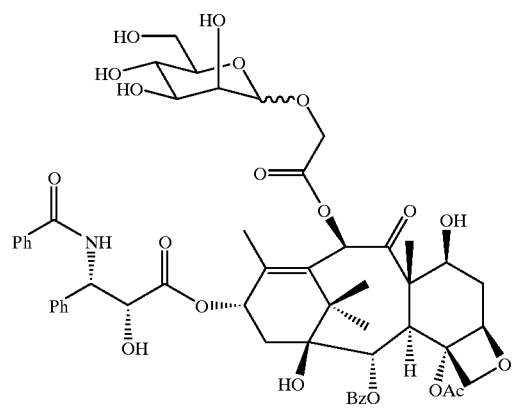

Galactosyloxyacetyl-7-docetaxel (hereinafter, abbreviated as "7-GAG-DT") of the following formula,

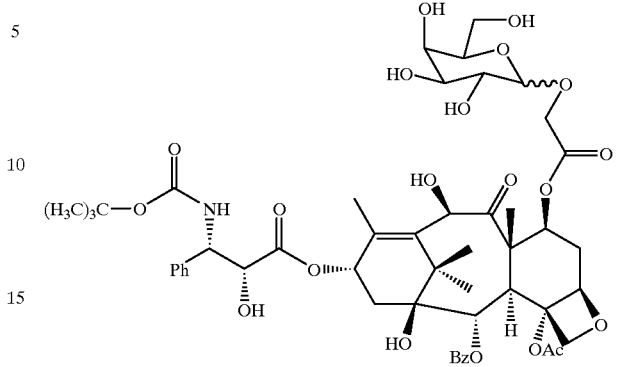

Mannosyloxyacetyl-7-docetaxel (hereinafter, abbreviated as "7-MAG-DT") of the following formula,

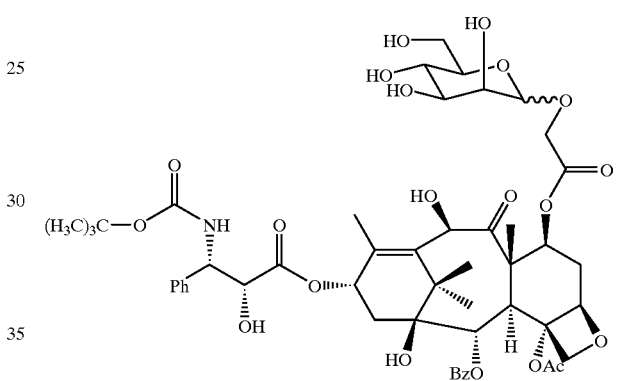

Galactosyloxyacetyl-10-docetaxel (hereinafter, abbreviated as "10-GAG-DT") of the following formula,

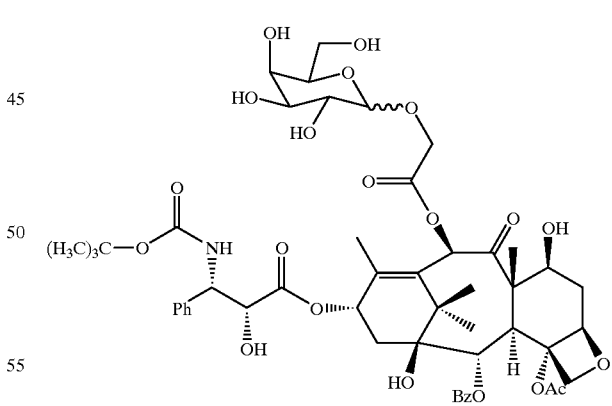

Mannosyloxyacetyl-10-docetaxel (hereinafter, abbreviated as "10-MAG-DT") of the following formula,

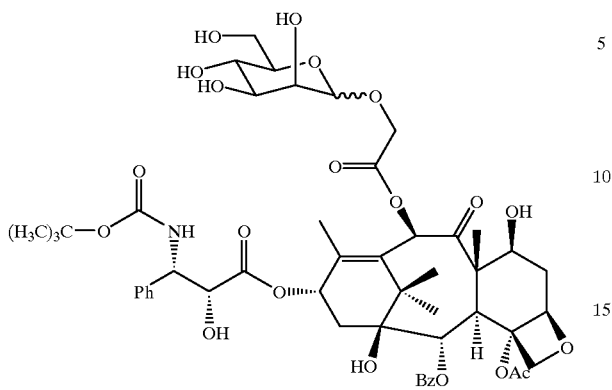

Galactosyloxyacetyl-7-baccatin III (hereinafter, abbreviated as "7-GAG, 10-deacetyl-baccatin-III") of the following formula,

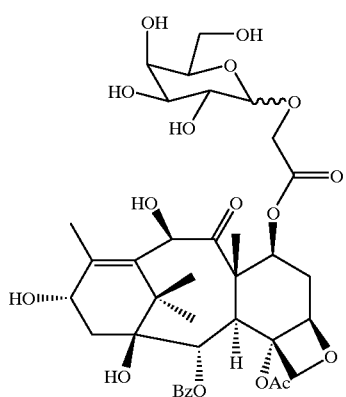

Mannosyloxyacetyl-7-baccatin III (hereinafter, abbreviated as "7-MAG, 10-deacetyl-baccatin-III") of the following formula,

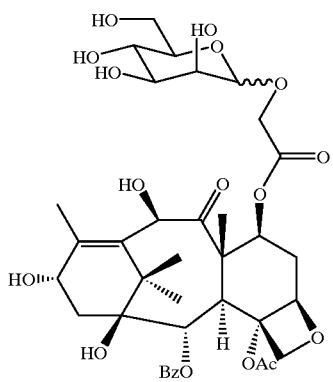

Galactosyloxyacetyl-10-baccatin III (hereinafter, abbreviated as "10-GAG-baccatin-III") of the following formula,

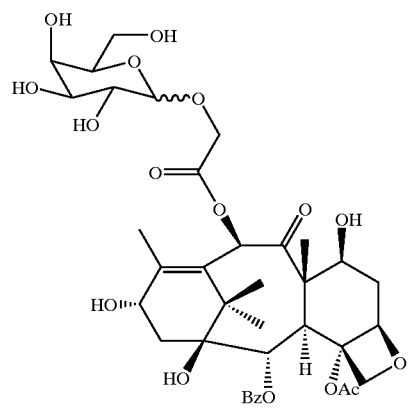

Mannosyloxyacetyl-10-baccatin III (hereinafter, abbreviated as "10-MAG-baccatin-III") of the following formula,

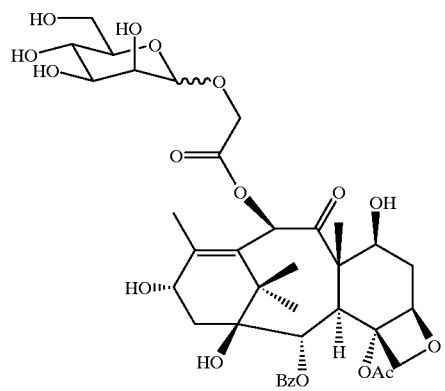

The taxoid derivatives of the present invention are those that contain any of paclitaxel, docetaxel and 10-deacetyl-baccatin III to which galactose or mannose is linked through a spacer, as described above.

Paclitaxel can be obtained by isolation from the bark of a yew tree (Taxus brevifolia) of North American growth by the method described in Kingston, D.G.I.: Pharmacol. Ther., 52, 1 (1992) and besides, chemically synthesized one (R. A. Holton: Europian Patent-A 400971, 1990) etc. can be used. Docetaxel can be derived from 10-deacetyl-baccatin III by the method described in Green, A. E. et al.: J. Org. Chem., 59, 1238 (1994). 10-Deacetyl-baccatin III, as described above, is a natural substance extracted from the yew tree of North American growth.

The reaction to link galactose ormannose to any of paclitaxel, docetaxel and 10-deacetyl-baccatin III through a spacer is carried out by use of tetrabenzyl acetyloxygalactoside or tetrabenzyl acetyloxymannoside. The tetrabenzyl acetyloxygalactoside or tetrabenzyl acetyloxymannoside is one obtained by linking a glycolate such as ethyl glycolate as a spacer to tetrabenzylgalactose or tetrabenzylmannose obtained respectively from galactose or mannose as a starting substance by a conventional method to form an ester compound and then deethylating the ester compound to form a carboxylic acid compound and they are represented by the following two formulae.

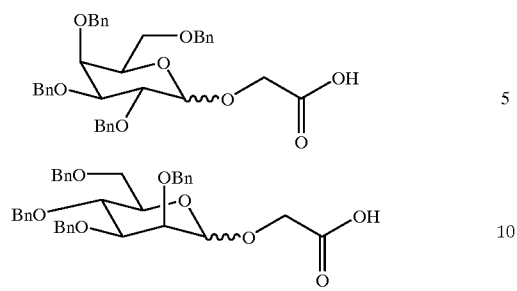

Next, an example of the production method for tetrabenzyl acetyloxygalactoside will be shown below.

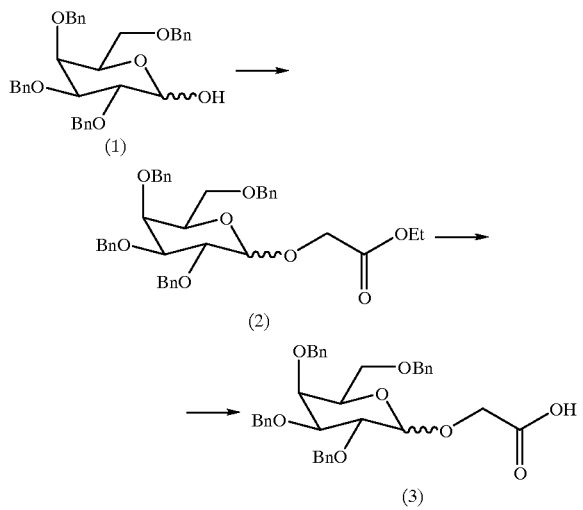

Tetrabenzylgalactose (1) obtained by a conventional method is reacted with ethyl glycolate together with p-toluenesulfonic acid in benzene at 0 to 150° C., preferably 110° C., for 0.5 to 50 hours, preferably 8 hours, to link ethyl glycolate to the 1-position thereof to obtain an ethyl ester compound (2). Thereafter, the compound (2) is treated in an alkali (for example, 6N NaOH) methanol-dioxane solution at room temperature to 100° C. for 0.5 to 50 hours, preferably 3 hours and then converted to acidic with hydrochloric acid (for example, 1N HCl) to effect deethylation to obtain a carboxylic acid compound (3). This substance is tetrabenzyl acetyloxygalactoside.

Next, an example of production method for tetrabenzyl acetyloxymannoside will be shown below.

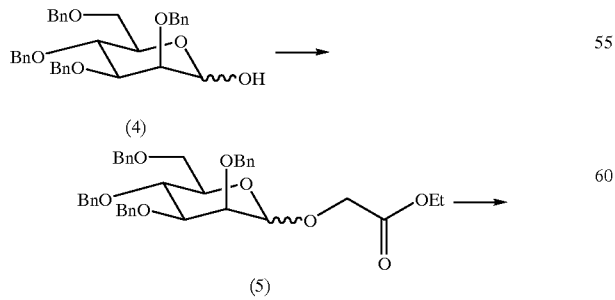

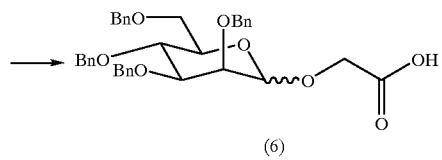

Tetrabenzylmannose (4) obtained by a conventional method is reacted with ethyl glycolate together with p-toluenesulfonic acid in benzene at 0 to 150° C., preferably 110° C., for 0.5 to 50 hours, preferably 8 hours, to link ethyl glycolate to the 1-position thereof to obtain an ethyl ester compound (5). Thereafter, the compound (5) is treated in an alkali (for example, 6N NaOH) methanol-dioxane solution at room temperature to 100° C. for 0.5 to 50 hours, preferably 3 hours and then converted to acidic with hydrochloric acid (for example, 1N HCl) to effect deethylation to obtain a carboxylic acid compound (6). This substance is tetrabenzyl acetyloxymannoside.

In the present invention, use is made of a glycolate such as ethyl glycolate as a spacer for the sugar donor. By changing the length of alkyl chain of this substance the length of spacer can be adjusted with ease. For example, 3-hydroxybutyric acid or the like can be used as a spacer.

The taxoid derivatives of the present invention can be produced by reacting any of paclitaxel, docetaxel, and 10-deacetyl-baccatin III with tetrabenzyl acetyloxygalactoside or tetrabenzyl acetyloxymannoside. Specific examples of the production method for taxoid derivatives include the methods illustrated by the following Reaction Schemes (I), (II), (III), (IV), and (V), respectively.

Reaction Scheme I

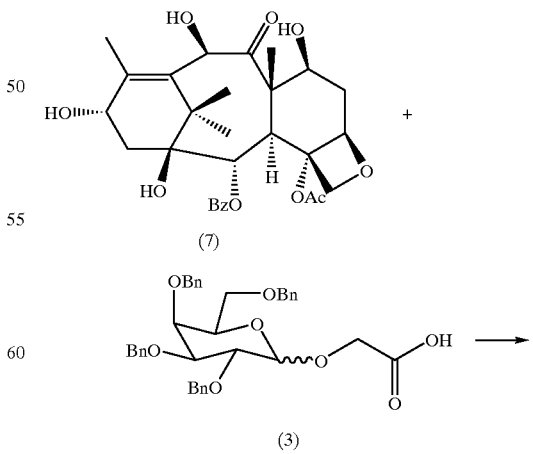

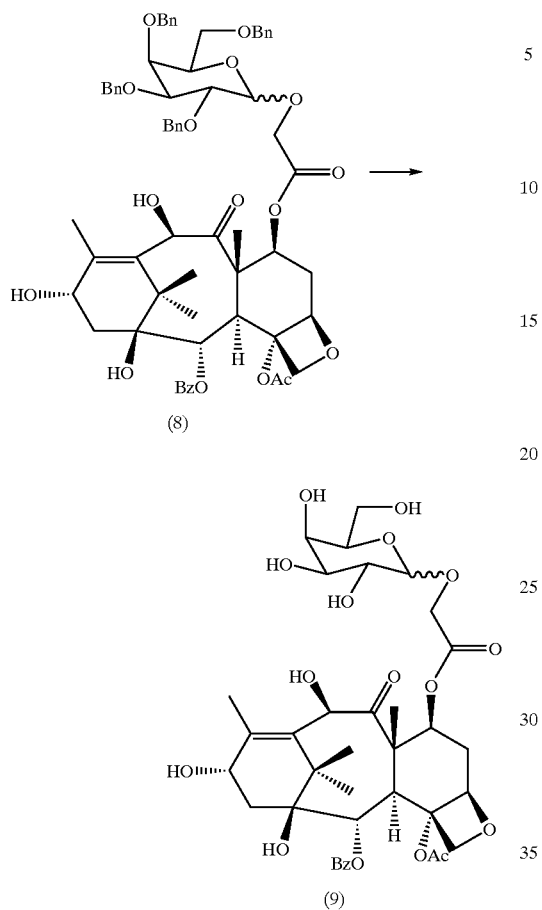
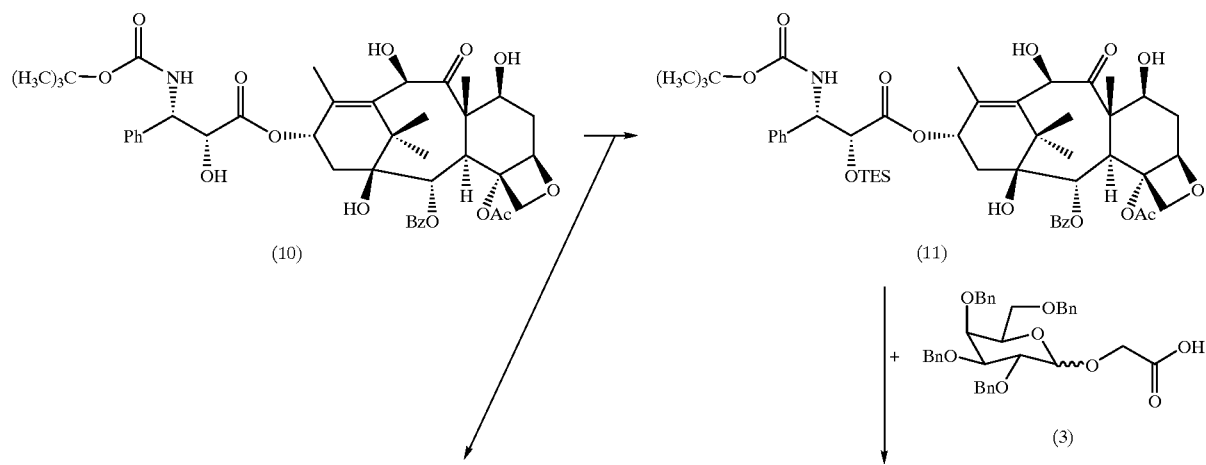
Reaction Scheme II

-continued
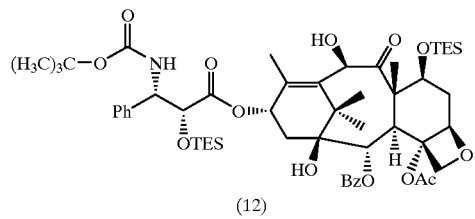
(12)
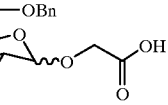
(3)
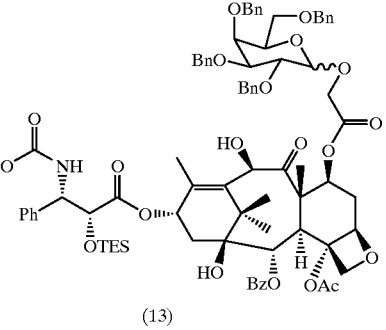
(13)
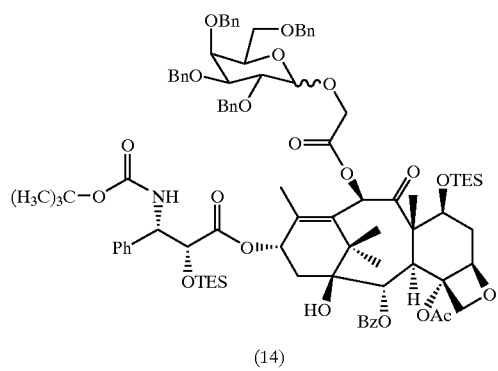
(14)
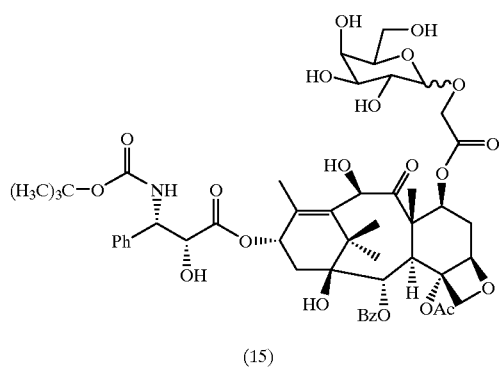
(15)
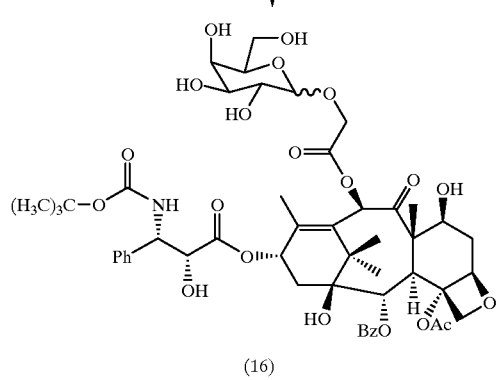
(16)
Reaction Scheme III
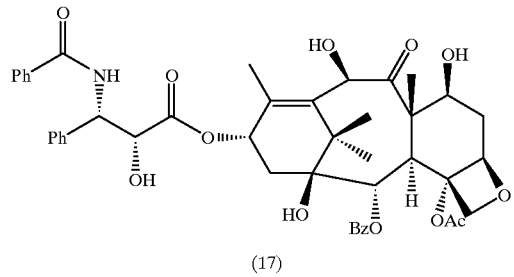
(17)
-continued
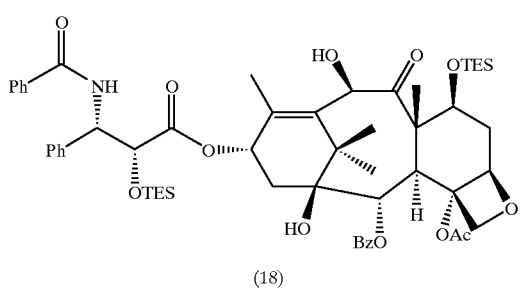
(18)

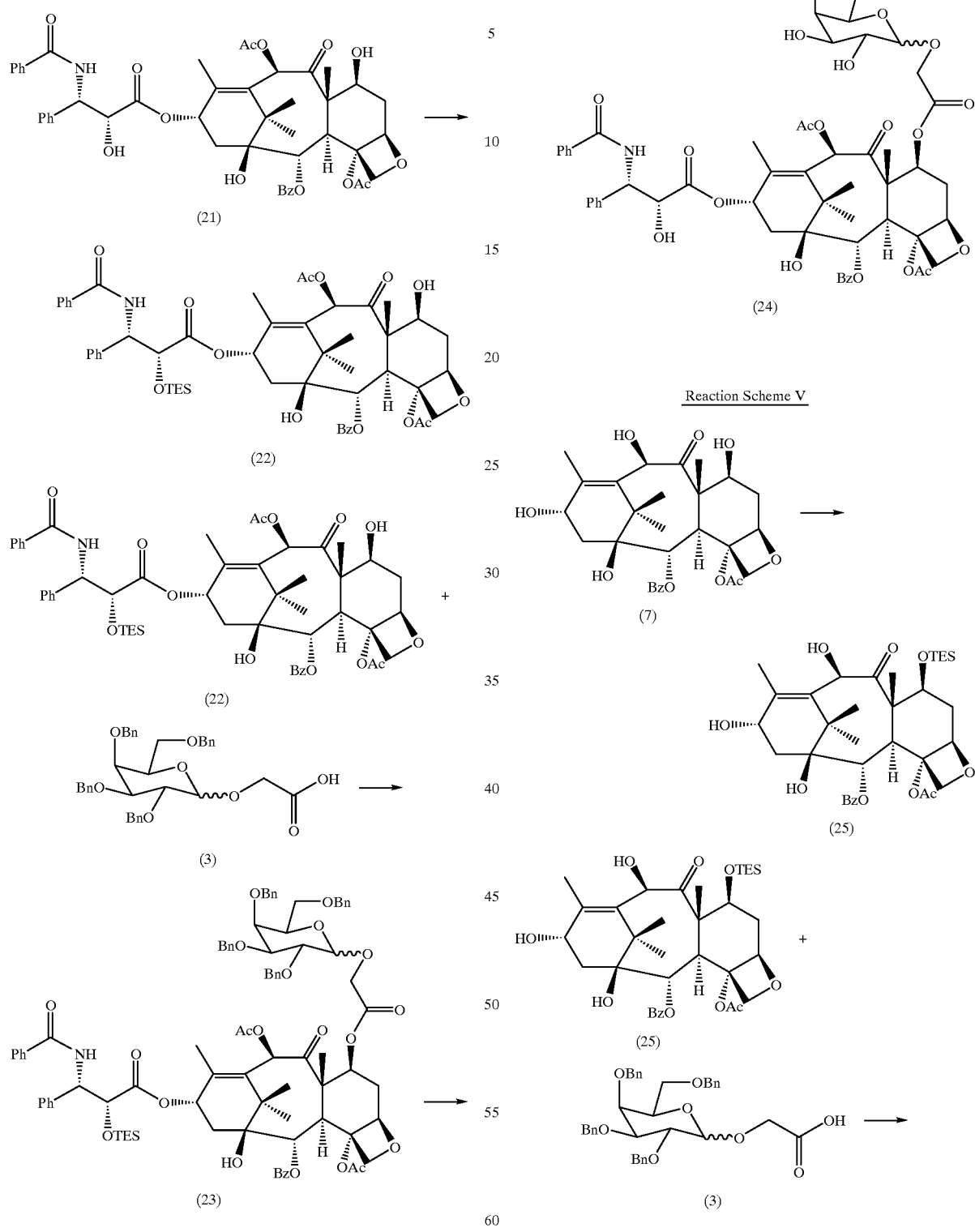

-continued

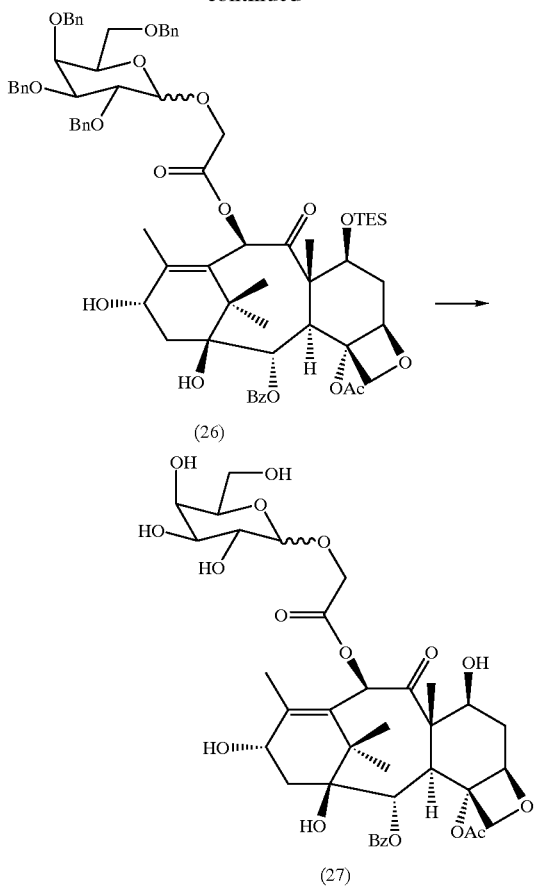

The method illustrated in Reaction Scheme (I) is to react 10-deacetyl-baccatin III (7) with tetrabenzyl acetyloxygalactoside (3) and then debenzylate the product and by this method 7-GAG-baccatin III (9) represented by the above formula can be obtained.

That is, 10-deacetyl-baccatin III (7) and tetrabenzyl acetyloxygalactoside (3) are reacted at room temperature for 0.5 to 100 hours, preferably 3 hours in argon atmosphere in the presence of a base such as 4-dimethylaminopyridine (DMAP), a condensing agent such as dicyclohexylcarbodiimide (DCC), and a solvent such as dichloromethane to obtain a glycoside compound (8).

Then, the compound (8), together with a catalyst such as palladium black and an acid such as acetic acid, is reacted by vigorously stirring in a hydrogen atmosphere at room temperature for 0. 5 to 100 hours, preferably 15 hours to allow debenzylation to occur to obtain 7-GAG, 10-deacetyl-baccatin III (9).

In the case where tetrabenzyl acetyloxymannoside is used instead of tetrabenzyl acetyloxygalactoside, 7-MAG, 10-deacetyl-baccatin III represented by the above formula can be obtained by a similar reaction.

The method illustrated in Reaction Scheme (II) is to react docetaxel, after protecting the 2'-position or the 2'- and 7-positions thereof with a triethylsilyl group, with tetrabenzyl acetyloxygalactoside (3) and then debenzylate and detriethylsilylate. By this method, 7-GAG-DT (15) or 10-GAG-DT (16) described above can be obtained.

That is, docetaxel (10) and a protecting agent such as chlorotriethylsilane (TESCl), a base such as imidazole, and a solvent such as dimethylformamide (DMF) are reacted in an argon atmosphere at room temperature for 0.5 to 50 hours, preferably 3 hours to protect the 2'-position or the 2'- and 7-positions thereof with a triethylsilyl group to obtain the compound (11) or compound (12).

Then, the obtained compound (11) or compound (12) and tetrabenzyl acetyloxygalactoside (3), a base such as DMAP, a condensing agent such as DCC, and a solvent such as dichloromethane are reacted in an argon atmosphere at room temperature for 0.5 to 100 hours, preferably 3 hours to obtain glycoside compound (13) or compound (14).

Thereafter, the compound (13) or compound (14) together with a catalyst such as palladium black and an acid such as acetic acid are reacted in a hydrogen atmosphere with vigorously stirring at roomtemperature for 0.5 to 100 hours, preferably 15 hours. Further, a solvent such as tetrahydrofuran (THF) and water are added and the mixture is allowed to react at room temperature for 0.5 to 50 hours, preferably 15 hours, to obtain the target compound (15) or compound (16). The compound (15) is 7-GAG-DT represented by the above formula and the compound (16) is 10-GAG-DT represented by the above formula.

In the case where tetrabenzyl acetyloxymannoside is used instead of tetrabenzyl acetyloxygalactoside, 7-MAG-DT and 10-MAG-DT represented respectively by the above formulae can be obtained by a similar reaction.

In the case where 10-deacetyl-paclitaxel (17) is used instead of docetaxel, 10-GAG-PT (20) represented by the above formula can be obtained according to Reaction Scheme (III) via the compound (19) obtained by reacting the compound (18), whose 2'- and 7-positions are protected, with tetrabenzyl acetyloxygalactoside (3). Similarly, in the case where tetrabenzyl acetyloxymannoside is used, 10-MAG-PT represented by the above formula can be obtained.

Similarly, in the case where paclitaxel (21) is used instead of docetaxel, 7-GAG-PT (24) represented by the above formula can be obtained according to Reaction Scheme (IV) via the compound (23) obtained by reacting the compound (22), whose 2'-position is protected, with tetrabenzyl acetyloxygalactoside (3). Similarly, in the case where tetrabenzyl acetyloxymannoside is used, 7-MAG-PT represented by the above formula can be obtained.

Further, in the case where 10-deacetyl-baccatin III (7) is used instead of docetaxel, 10-GAG-baccatin III (27) represented by the above formula can be obtained according to Reaction Scheme (V) via the compound (26) obtained by reacting the compound (25), whose 7-position is protected, with tetrabenzyl acetyloxygalactoside (3). Similarly, in the case where tetrabenzyl acetyloxymannoside is used, 10-MAG-baccatin III represented by the above formula can be obtained.

Anomers of the taxoid derivatives of the present invention can be removed by application of liquid chromatography using a carrier containing silica gel as a matrix, such as ODS, so that purified preparation utilizable as a medicine can be obtained.

Each of these taxoid derivatives has an improved solubility in water; paclitaxel has a solubility of 0.4 μg/ml in contrast to 67.8 μg/ml (169 times) for 7-GAG-PT, 103.0 μg/ml (257 times) for 7-MAG-PT, 481.7 μg/ml (1204 times) for 10-GAG-DT (α-anomer), 301.4 μg/ml (753 times) for 10-GAG-DT (β-anomer), and 1038.6 μg/ml (2596 times) for 10-MAG-DT (α-anomer). The taxoid derivatives have improved solubility in alcohols also.

Upon in vivo administration of the taxoid derivatives to mice who have been implanted with P388 leukemia cells, 10-MAG-DT showed a survival effect substantially equivalent to that of paclitaxel and 10-GAG-DT showed a survival effect of 1.2 times as compared with paclitaxel. At that time, the body weight of mice decreased abruptly when paclitaxel was administered whereas the taxoid derivatives showed no decrease in body weight. The results obtained indicate that they are excellent also in safety. As described above, the physiological activity of each taxoid derivative is equivalent to or higher than that of paclitaxel and safety thereof is also excellent, so that the taxoid derivatives of the present invention can be used as an antitumor agent. Galactose and mannose have affinity for living body, particularly liver cells, and hence the taxoid derivatives of the present invention are effective in the therapy of liver tumors.

Next, the present invention will be explained in more detail by examples. However, the present invention is not limited thereto.

PRODUCTION EXAMPLE 1

10 mmol of tetrabenzylgalactose (1) obtained by a conventional method, 30 mmol of ethyl glycolate, 1 mmol of p-toluenesulfonic acid, and 10 ml of benzene were reacted at 110° C. for 8 hours to obtain compound (2) ($C_{38}H_{42}O_8$, molecular weight: 626.74).

Then, 3 mmol of this compound was reacted with 10 ml of 6N NaOH, 10 ml of methanol, and 15 ml of dioxane at room temperature to 100° C. for 3 hours. Thereafter, the reaction mixture was transferred into 80 ml of 1N HCl to effect deethylation to obtain compound (3), i.e., a carboxylic acid compound ($C_{36}H_{38}O_8$, molecular weight: 598.69).

PRODUCTION EXAMPLE 2

10 mmol of tetrabenzylmannose (4) obtained by a conventional method, 30 mmol of ethyl glycolate, 1 mmol of p-toluenesulfonic acid, 10 ml of benzene were reacted at 110° C. for 8 hours to obtain compound (5) ($C_{38}H_{42}O_8$, molecular weight: 626.74).

Then, 3 mmol of this compound was reacted with 10 ml of 6N NaOH, 10 ml of methanol, and 15 ml of dioxane at from room temperature to 100° C. for 3 hours. Thereafter, the reaction mixture was transferred into 80 ml of 1N HCl to effect deethylation to obtain compound (6), i.e., a carboxylic acid compound ($C_{36}H_{38}O_8$, molecular weight: 598.69).

EXAMPLE 1

0.3 mnmol of 10-deacetyl-baccatin III (7), 0.6 mmol of tetrabenzyl acetyloxygalactoside (3) obtained in Production Example 1, 1 mnmol of 4-dimethylaminopyridine (DMAP), 1 mmol of dicyclohexylcarbodiimide (DCC) , and 5 ml of dichloromethane were reacted in an argon atmosphere at room temperature for 3 hours to obtain a compound (8) ($C_{65}H_{72}O_{17}$, molecular weight: 1, 125.27) , which was glycosylated at the 7-position.

0.2 mmol of the compound (8) together with 100 mg of palladium black and 3 ml of acetic acid were reacted in a hydrogen atmosphere at room temperature for 15 hours with vigorous stirring to effect debenzylation to obtain 7-GAG, 10-deacetyl-baccatin III (9) ($C_{37}H_{48}O_{17}$, molecular weight: 764.78). This compound was produced according to Reaction Scheme (I).

EXAMPLE 2

The tetrabenzyl acetyloxymannoside (6) obtained in Production Example 2 instead of tetrabenzyl acetyloxygalactoside was reacted with 10-deacetyl-baccatin III in the same manner as in Example 1 above to obtain a compound (28). Thereafter, the benzyl group was removed to obtain 7-MAG, 10-deacetyl-baccatin III (29) ($C_{37}H_{48}O_{17}$, molecular weight: 764.78). This compound was produced according to Reaction Scheme (VI).

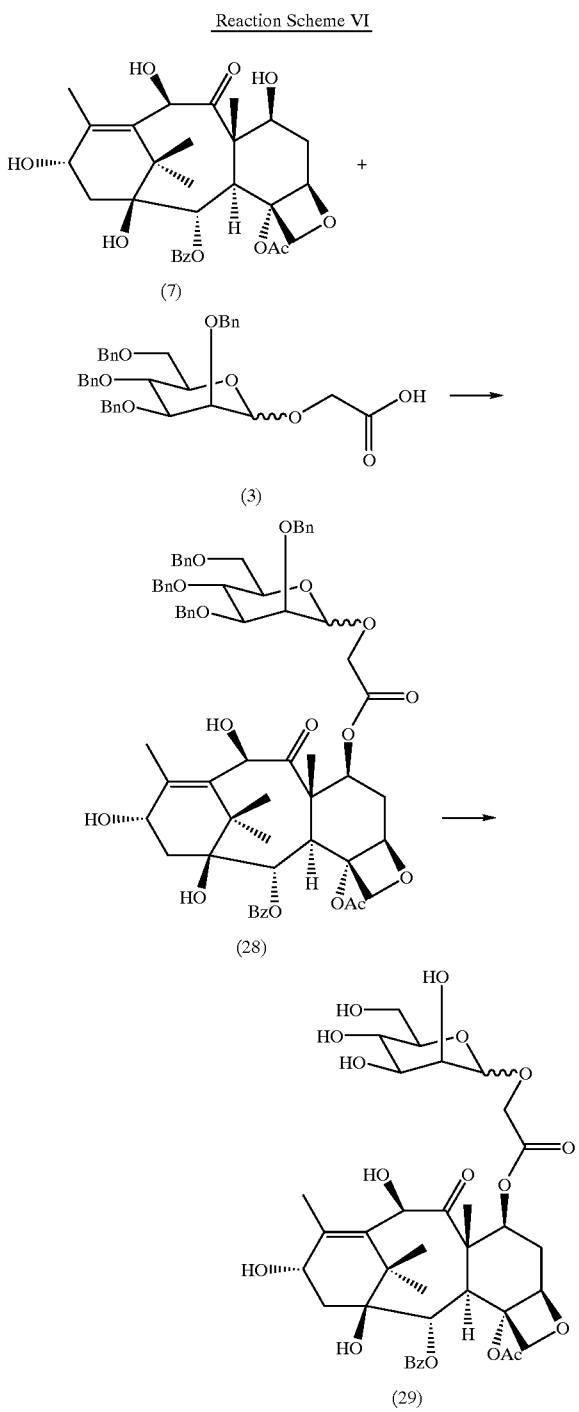

EXAMPLE 3

0.5 mmol of docetaxel (10), 1 mmol of chlorotriethylsilane (TESCl), 1 mmol of imidazole, and 5 ml of dimethylformamide (DMF) were reacted in an argon atmosphere at room temperature for 3 hours to protect the 2'-position or the 2'- and 7-positions of docetaxel with a triethylsilyl group (TES) to obtain the compound (11) and the compound (12).

0.3 mmol of the compound (11) and of compound (12), 0.6 mmol of the tetrabenzyl acetyloxygalactoside (3) obtained in Production Example 1, 1 mmol of DMAP, 1 mmol of DCC, and 5 ml of dichloromethane were reacted in an argon atmosphere at room temperature for 3 hours to obtain glycoside compounds (13) and (14).

0.2 mmol of the obtained compounds (13) and (14), 100 mg of palladium black, and 3 ml of acetic acid were reacted in a hydrogen atmosphere at room temperature for 15 hours with vigorous stirring. Further, 1 ml of tetrahydrofuran (THF) and 1 ml of water were added thereto and reaction was carried out at room temperature for 15 hours to obtain 7-GAG-DT (15) ($C_{51}H_{65}NO_{21}$, molecular weight: 1,028.07) and 10-GAG-DT (16) ($C_{51}H_{65}NO_{21}$, molecular weight: 1,028.07).

Then, using a column (φ20 mm×250 mm) packed with silica gel (trade name: ODS, manufactured by YMC Co. Ltd.) and methanol as a mobile phase, 7-GAG-DT and 10-GAG-DT were purified for every anomer. The compounds were produced according to Reaction Scheme (II).

EXAMPLE 4

Using the tetrabenzyl acetyloxymannoside (6) obtained in Production Example 2 instead of tetrabenzyl acetyloxygalactoside, glycoside forms could be obtained in the same manner as in Example 3 above.

That is, the compounds (11) and (12) obtained by protecting the 2'-position or 2'- and 7-positions of docetaxel with TES were reacted with the tetrabenzyl acetyloxymannoside (6) to obtain compounds (30) and (31). Thereafter, the benzyl groups and TES were removed from the compounds (30) and (31) to obtain 7-MAG-DT (32) ($C_{51}H_{65}N_{21}$, molecular weight: 1,028.07) and 10-MAG-DT (33) ($C_{51}H_{65}NO_{21}$, molecular weight: 1,028.07).

Then, 7-MAG-DT and 10-MAG-DT were purified in a column. These compounds were produced according to the following Reaction Scheme (VII).

Reaction Scheme VII

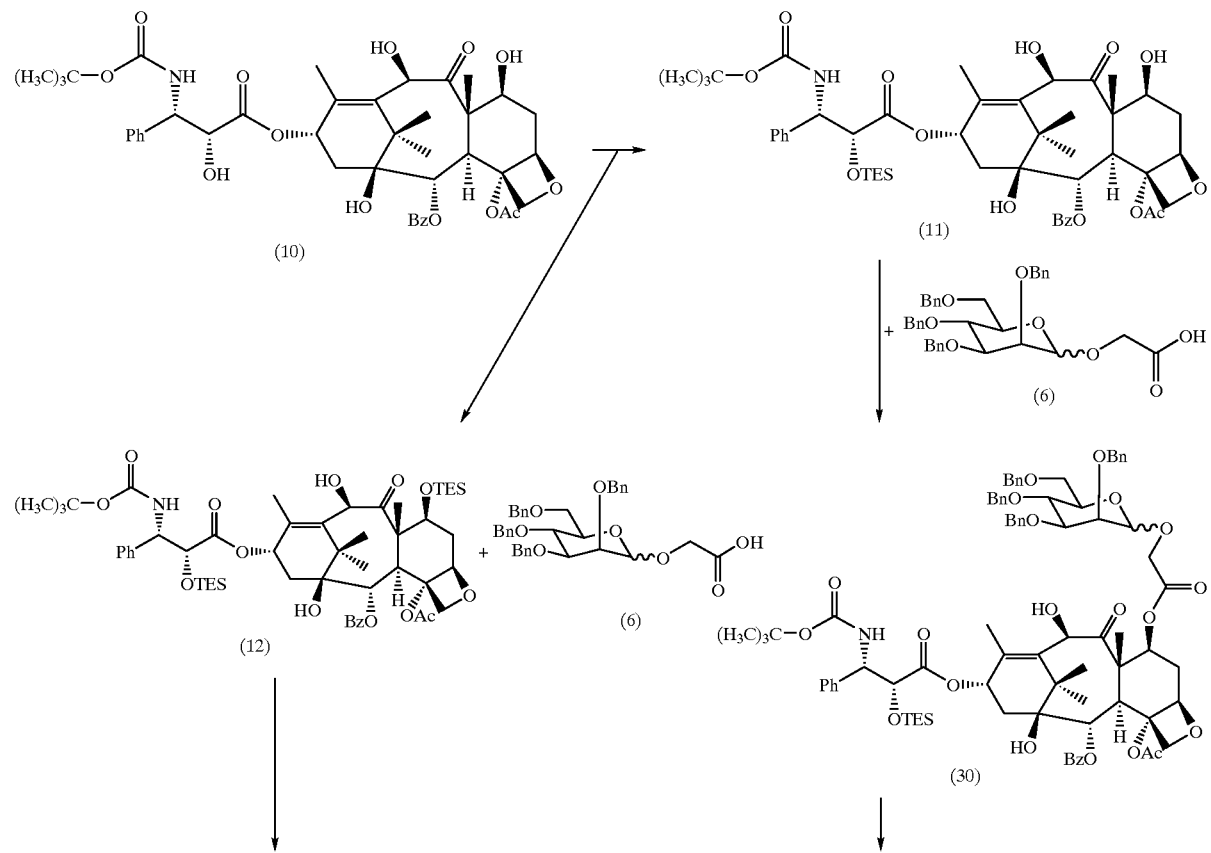

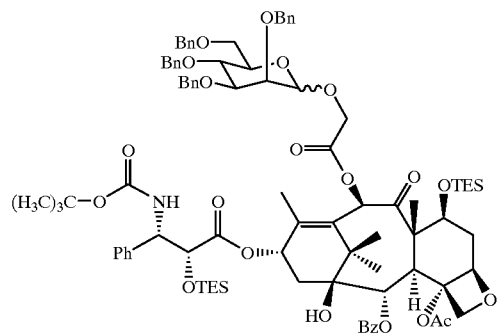

(31)

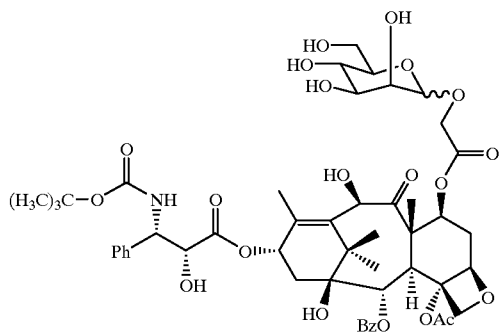

(32)

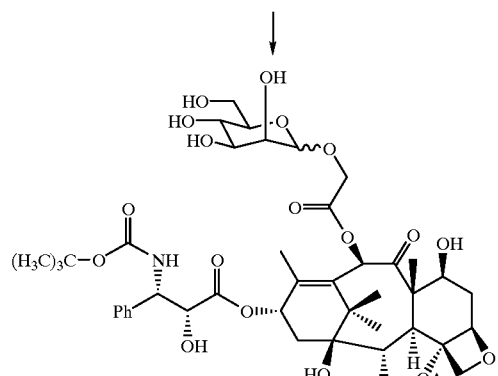

(33)

EXAMPLE 5

Using 10-deacetyl-paclitaxel (17) instead of docetaxel, compound (18) was obtained in the same manner as in Example 3 above by protecting the 2'- and 7-positions of 10-deacetyl-paclitaxel with TES groups. Thereafter, the obtained compound was reacted with the tetrabenzyl acetyloxygalactoside (3) obtained in Production Example 1 to obtain compound (19). Thereafter, the benzyl groups and TES groups were removed from the compound (19) to obtain 10-GAG-PT (20) ($C_{53}H_{61}NO_{20}$, molecular weight: 1,032.06). This compound was produced according to Reaction Scheme (III).

EXAMPLE 6

Using the tetrabenzyl acetyloxymannoside (6) obtained in Production Example 2 instead of tetrabenzyl acetyloxygalactoside, glycoside forms could be obtained in the same manner as in Example 5 above.

That is, the compound (18) was obtained by protecting the 2'- and 7-positions of paclitaxel with TES groups. Then, the obtained compound was reacted with the tetrabenzyl acetyloxymannoside (6) obtained in Production Example 2 to obtain compound (34). Thereafter, the benzyl groups and TES groups were removed from the compound (34) to obtain 10-MAG-PT (35) ($C_{53}H61NO_{20}$, molecular weight: 1,032.06). This compound was produced according to the following Reaction Scheme (VIII).

Reaction Scheme VIII

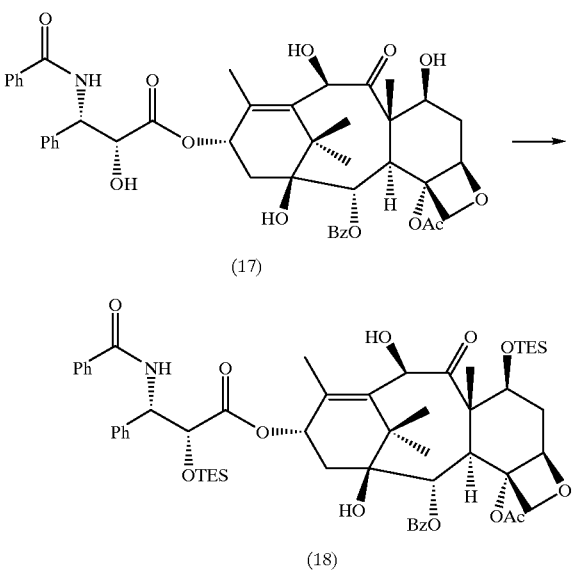

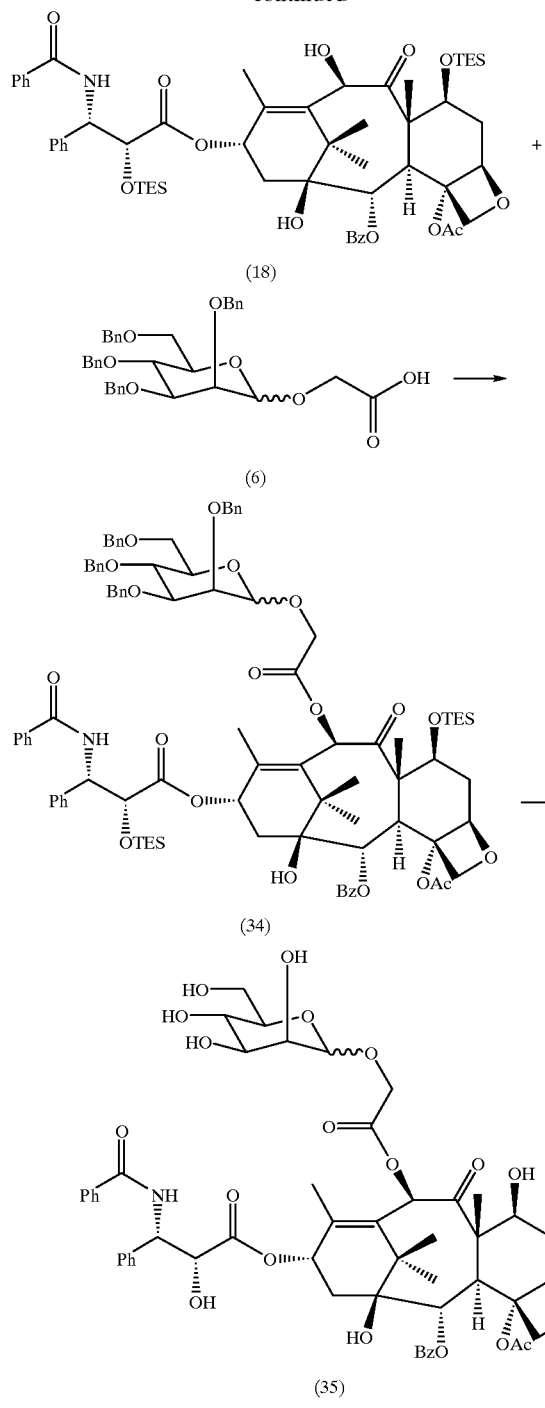

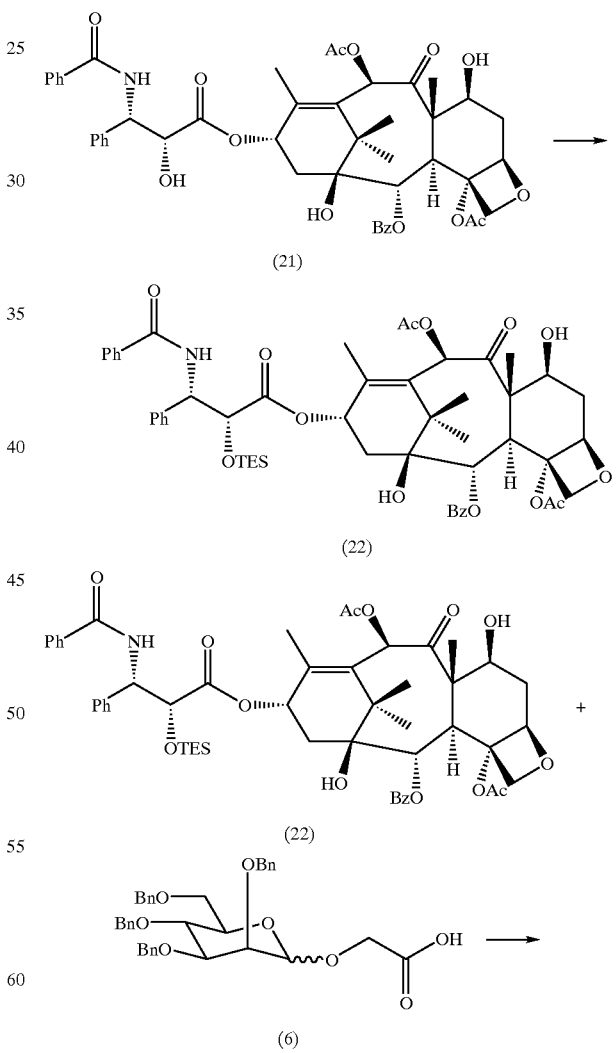

groups and TES group were removed from the compound (23) to obtain 7-GAG-PT (24) ($C_{55}H_{63}NO_{21}$, molecular weight: 1,074.10). This compound was produced according to Reaction Scheme (IV).

EXAMPLE 8

Using the tetrabenzyl acetyloxymannoside (6) obtained in Production Example 2 instead of tetrabenzyl acetyloxygalactoside, glycoside forms could be obtained in the same manner as in Example 7 above.

That is, the compound (22) was obtained by protecting the 2'-position of paclitaxel with TES group. Then, the obtained compound was reacted with the tetrabenzyl acetyloxymannoside (6) obtained in Production Example 2 to obtain a compound (36). Thereafter, the benzyl groups and TES group were removed from the compound (36) to obtain 7-MAG-PT (37) ($C_{55}H_{63}NO_{21}$, molecular weight: 1,074.10). This compound was produced according to the following Reaction Scheme (IX).

EXAMPLE 7

Using paclitaxel (21) instead of docetaxel, a compound (22) was obtained by protecting the 2'-position of paclitaxel with TES group in the same manner as in Example 3 above. Thereafter, the obtained compound was reacted with the tetrabenzyl acetyloxygalactoside (3) obtained in Production Example 1 to obtain a compound (23). Thereafter, the benzyl

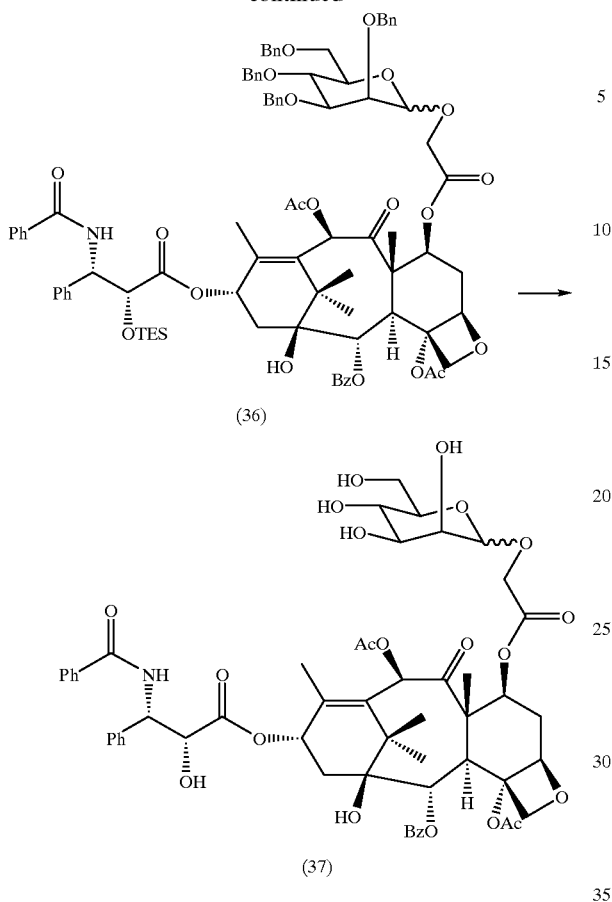

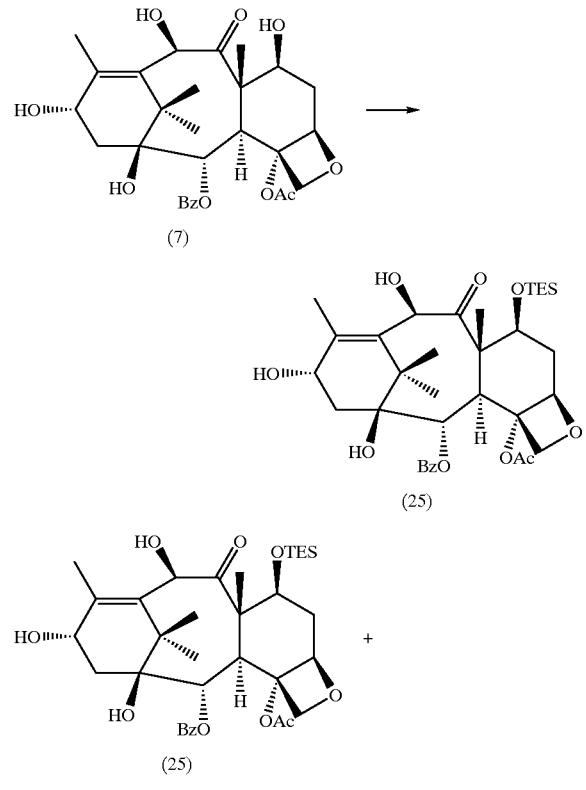

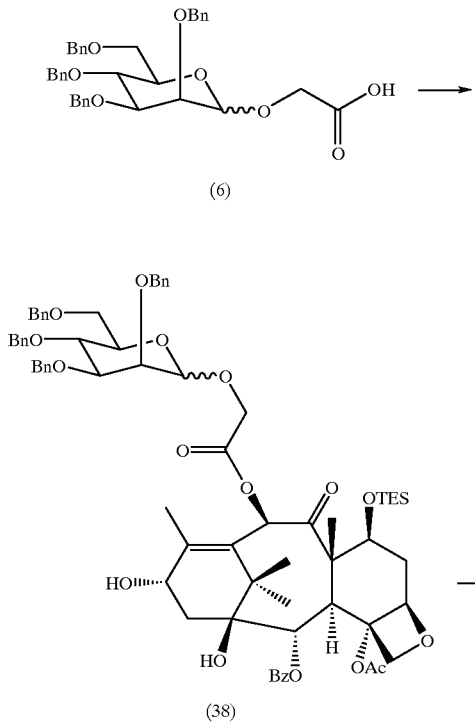

EXAMPLE 9

Using 10-deacetyl-baccatin III (7) instead of docetaxel, a compound (25) was obtained by protecting the 7-position of 10-deacetyl-baccatin III with TES group in the same manner as in Example 3 above. Thereafter, the obtained compound was reacted with the tetrabenzyl acetyloxygalactoside (3) obtained in Production Example 1 to obtain a compound (26). Thereafter, the benzyl groups and TES group were removed from the compound (26) to obtain 10-GAG-baccatin III (27) ($C_{37}H_{48}NO_{17}$, molecular weight: 764.78). This compound was produced according to Reaction Scheme (V).

EXAMPLE 10

Using the tetrabenzyl acetyloxymannoside (6) obtained in Production Example 2 instead of tetrabenzyl acetyloxygalactoside, glycoside forms could be obtained in the same manner as in Example 9 above.

That is, the compound (25) was obtained by protecting the 7-position of 10-deacetyl-baccatin III with TES group. Then, the obtained compound was reacted with the tetrabenzyl acetyloxymannoside (6) obtained in Production Example 2 to obtain a compound (38). Thereafter, the benzyl groups and TES group were removed from the compound (38) to obtain 10-MAG-baccatin III (39) ($C_{37}H_{48}NO_{17}$, molecular weight: 764.78). This compound was produced according to the following Reaction Scheme (X).

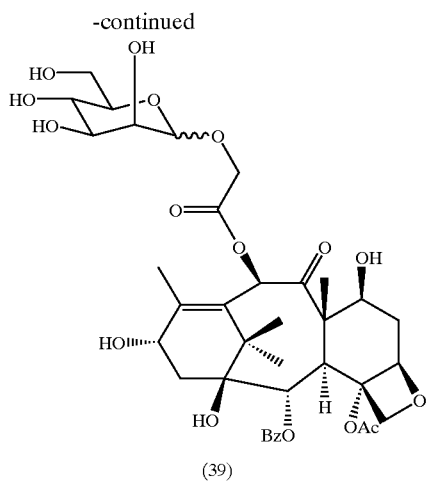

(39)

EXAMPLE 11

10 mg of each of paclitaxel, 7-GAG-PT, 7-MAG-PT, 10-GAG-DT (α-anomer), 10-GAG-DT (β-anomer) and 10-MAG-DT (α-anomer) was weighed. To those were added 5 ml of water and the mixture was stirred for 18 hours. After completion of the stirring, supernatant was filtered through a membrane filter (0.45 μm), and the filtrate was analyzed by HPLC. As a result, the solubility of each compound in water was as shown in Table 1. The conditions of HPLC analysis were as follows.

Column: Taxil 5μ (4.6×250 mm) manufactured by Metachem Solvent: MeOH/H$_2$O (80/20) Flow rate: 0.5 ml/min Detector: Photodiode array detector (230 nm) Injection amount: 20 μl.

TABLE 1

| Sample | Solubility (μg/ml) |
| --- | --- |
| Paclitaxel | 0.4 |
| 7-GAG-PT | 67.8 |
| 7-MAG-PT | 103.0 |
| 10-GAG-DT (α-anomer) | 481.7 |
| 10-GAG-DT (β-anomer) | 301.4 |
| 10-MAG-DT (α-anomer) | 1,038.6 |

As will be apparent from the table, the solubility of taxoid derivatives was increased by leaps and bounds as compared with paclitaxel. The taxoid derivatives were not decomposed in aqueous solutions and were stable.

EXAMPLE 12

Antitumor tests were carried out on paclitaxel, 10-GAG-DT (α-anomer), 10-GAG-DT (β-anomer) and 10-MAG-DT (α-anomer) using mice implanted with P388 leukemia cells.

The mice used were 7 weeks age CDF1 mice (male). P388 leukemia cells subcultured in DBA/2 mouse abdominal cavity were injected in the abdominal cavity in an amount of 10$_6$ cells per mouse. In the case of paclitaxel, samples were dissolved in a solution of ethanol:cremophor=1:1 to a concentration of 6 mg/ml and then diluted 30 times with physiological saline. This was administered intraperitoneally in a dose of 0.1 ml/10 g mouse/time. In the case of taxoid derivatives, samples were dissolved in a solution of ethanol:cremophor=1:1 to a concentration of 60 mg/ml and then diluted 30 times with physiological saline. This was administered intraperitoneally in a dose of 0.1 ml/10 g mouse/time.

The tests were performed by administering the sample for consecutive 5 days starting from the day next to the day when the P388 leukemia cells were injected into the abodominal cavity and observing survival days and change in body weight.

Table 2 shows the results of survival days and FIG. 1 shows changes in body weight.

TABLE 2

| Treatment | Number of Animals | Survival Day by Individual | Median of Survival Days | % T/C[a]) |
| --- | --- | --- | --- | --- |
| No treatment control | 10 | 7 7 7 7 7 7 7 7 7 10 | 7 | — |
| Paclitaxel solvent control | 10 | 7 7 7 7 7 7 7 7 7 7 | 7 | 100 |
| Paclitaxel 20 mg/kg | 9 | 9 9 10 10 10 10 11 11 12 | 10 | 143 |
| Paclitaxel derivative solvent control | 10 | 7 7 7 7 7 7 7 7 7 7 | 7 | 100 |
| 10-MAG-DT (α-anomer) 20 mg/kg | 10 | 8 9 9 9 9 9 9 10 11 15 | 9 | 129 |
| 10-GAG-DT (α-anomer) 20 mg/kg | 10 | 10 11 11 11 12 12 12 12 13 14 | 12 | 171 |
| 10-GAG-DT (β-anomer) 20 mg/kg | 10 | 11 11 11 11 12 12 12 12 13 20 | 12 | 171 |

[a])Median of survival days of each treated group (day) × 100/Median of survival days of control group (day)

From the table, it is apparent that the median of survival days was 7 days for the control group while it was 10 days for paclitaxel group, 9 days for 10-MAG-DT (α-anomer) group, 12 days 10-GAG-DT (α-anomer) group, and 12 days for 10-GAG-DT (β-anomer) group. From this it follows that the taxoid derivatives have antitumor activity equivalent to or higher than that of paclitaxel. In particular, 10-GAG-DT has excellent antitumor activity.

Furthermore, as will be apparent from the figure, the paclitaxel group showed an abrupt decrease in body weight after the administration in contrast to the taxoid derivatives, which showed substantially no change in body weight, so that the latter are also excellent in safety.

Industrial Applicability

The present invention provides taxoid derivatives having increased solubility in water and improved physiological activity and production method therefor. The taxoid derivatives alleviate burden imposed on patients and their utilization as an effective therapeutic drug can be expected.

What is claimed is:

1. A taxoid derivative comprising any one of paclitaxel, docetaxel and 10-deacetyl-baccatin III to which galactose or mannose is linked through a glycolate which is a spacer.

2. The taxoid derivative of claim 1, wherein the taxoid derivative is galactosyloxyacetyl-7-paclitaxel represented by the following formula

3. The taxoid derivative of claim 1, wherein the taxoid derivative is mannosyloxyacetyl-7-paclitaxel represented by the following formula

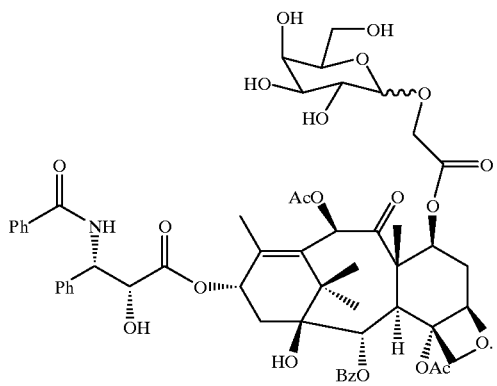

4. The taxoid derivative of claim 1, wherein the taxoid derivative is galactosyloxyacetyl-10-paclitaxel represented by the following formula

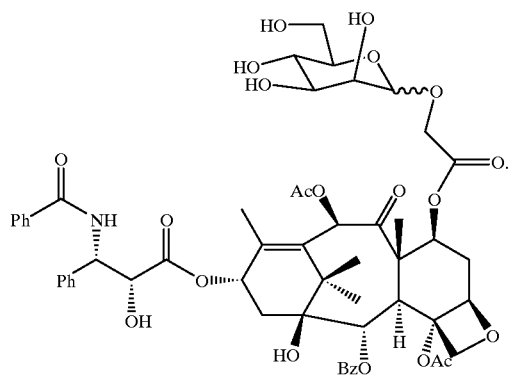

5. The taxiod derivative of claim 1, wherein the taxoid derivative is mannosyloxyacety-10 paclitaxel represented by the following formula

6. The taxoid derivative of claim 1, wherein the taxoid derivative is galactosyloxyacetyl-7-docetaxel represented by the following formula

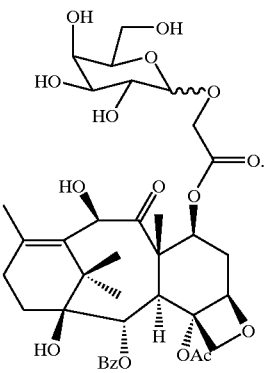

7. The taxoid derivative of claim 1, wherein the taxoid derivative is mannosyloxyacetyl-7docetaxel represented by the following formula

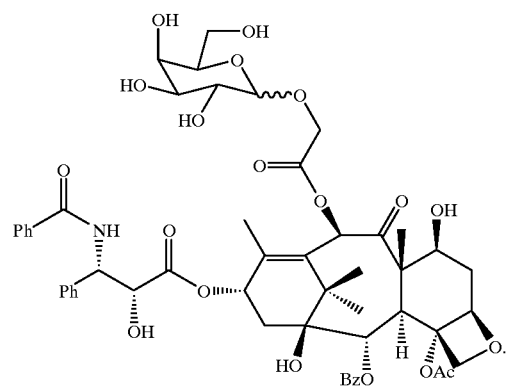

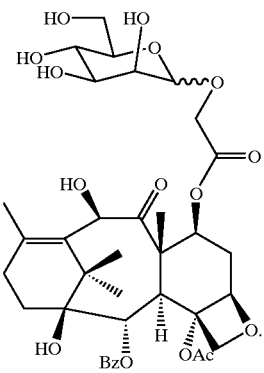

8. The taxiod derivative of claim 1, wherein the taxoid derivative is galactosyloxyacetyl-10-docetaxel represented by the following formula

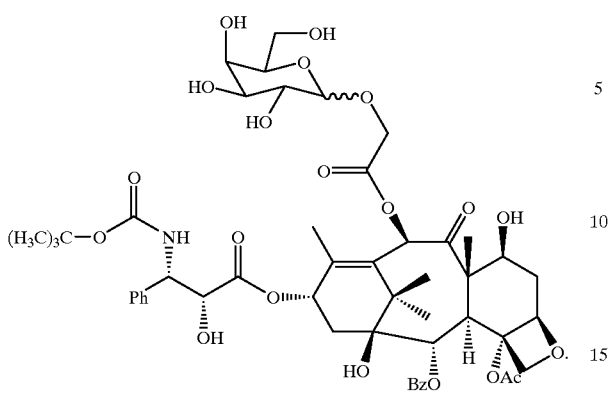

9. The taxiod derivative of claim 1, wherein the taxoid derivative is mannosyloxyacetyl-10-docetaxel represented by the following formula

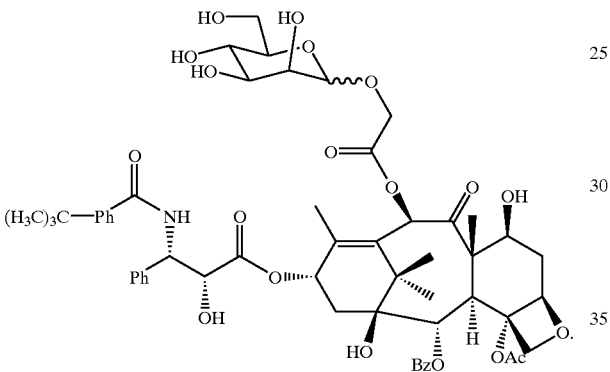

10. The taxoid derivative of claim 1, wherein the taxoid derivative is galactosyloxyacetyl-7-baccatin III represented by the following formula

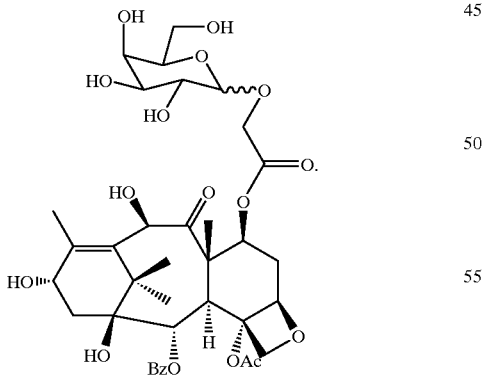

11. The taxoid derivative of claim 1, wherein the taxoid derivative is mannosyloxyacetyl-7-baccatin III represented by the following formula

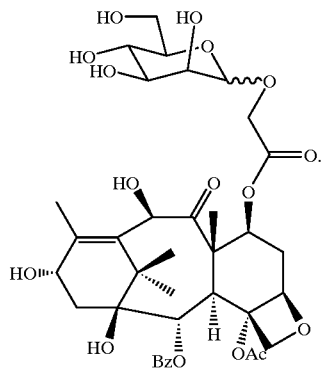

12. The taxoid derivative of claim 1, wherein the taxoid derivative is galactosyloxyacetyl-10-baccatin III represented by the following formula

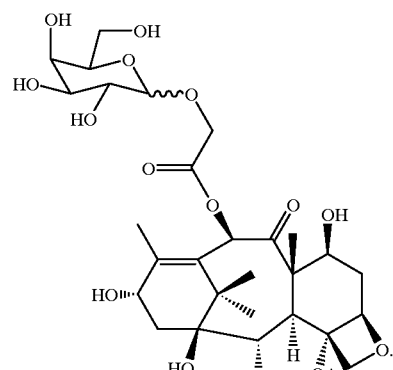

13. The taxoid derivative of claim 1, wherein the taxoid derivative is mannosyloxyacetyl-10-baccatin III represented by the following formula

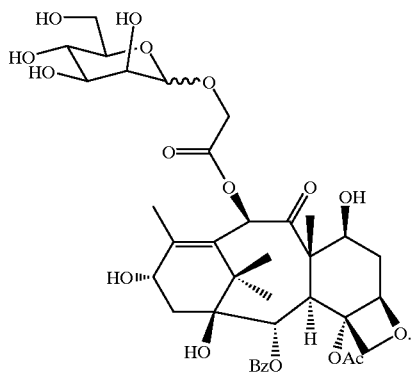

14. A method for producing the taxoid derivative of claim 6, comprising after protecting a hydroxyl group at the 2'-position of paclitaxel or docetaxel with chlorotriethylsilane, reacting the product with tetrabenzyl acetyloxygalactoside represented by the following formula, and then subjecting the prodcut to debenzylation or detriethylsilyation reaction

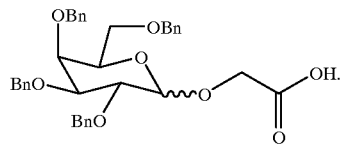

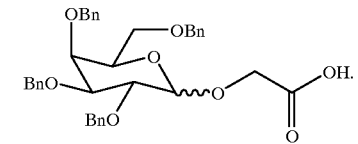

15. A method for producing the taxoid derivative of claim 7, comprising after protecting a hydroxyl group at the 2'-position of paclitaxel or docetaxel with chlorotriethylsilane, reacting the product with tetrabenzyl acetyloxymannoside represented by the following formula, and then subjecting the prodcut to debenzylation or detriethylsilyation reaction

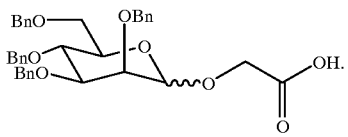

16. A method for producing the taxoid derivative of claim 8, comprising after protecting hydroxyl groups at the 2'- and 7-positions of paclitaxel or docetaxel, respectively, with chlorotriethylsilane, reacting the product with tetrabenzyl acetyloxygalactoside represented by the following formula, and then subjecting the product to debenzylation or detriethylsilyation reaction

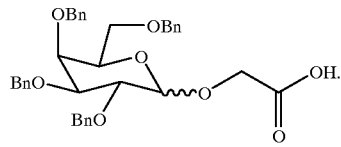

17. A method for producing the taxoid derivative of claim 9, comprising after protecting hydroxyl groups at the 2'- and 7-positions of 10-deacetyl-paclitaxel or docetaxel, respectively, with chlorotriethylsilane, reacting the product with tetrabenzyl acetyloxymannoside represented by the following formula, and then subjecting the product to debenzylation or detriethylsilyation reaction

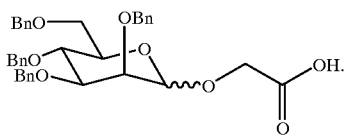

18. A method for producing the taxoid derivative of claim 2, comprising after protecting a hydroxyl group at the 2'-position of paclitaxel or docetaxel with chlorotriethylsilane, reacting the product with tetrabenzyl acetyloxygalactoside represented by the following formula, and then subjecting the product to debenzylation or detriethylsilylation reaction 19. A method for producing the taxoid derivative of claim 3, comprising after protecting a hydroxyl group at the 2'-position of paclitaxel or docetaxel with chlorotriethylsilane, reacting the product with tetrabenzyl acetyloxymannoside represented by the following formula, and then subjecting the product to debenzylation or detriethylsilylation reaction

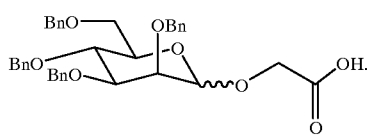

20. A method for producing the taxoid derivative of claim 4, comprising after protecting hydroxyl groups at the 2'- and 7-positions of 10-deacetyl-paclitaxel or docetaxel, respectively, with chlorotriethylsilane, reacting the product with tetrabenzyl acetyloxygalactoside represented by the following formula, and then subjecting the product to debenzylation or detriethylsilylation reaction

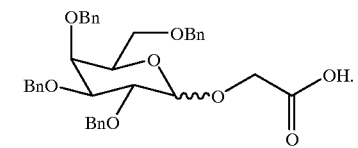

21. A method for producing the taxoid derivative of claim 5, comprising after protecting hydroxyl groups at the 2'- and 7-positions of 10-deacetyl-paclitaxel or docetaxel, respectively, with chlorotriethylsilane, reacting the product with tetrabenzyl acetyloxymannoside represented by the following formula, and then subjecting the product to debenzylation or detriethylsilylation reaction

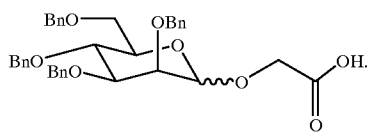

22. A method for producing the taxoid derivative of claim 12, comprising after protecting a hydroxyl group at the 7-position of 10-deacetyl-baccatin III with chlorotriethylsilane, reacting the product with tetrabenzyl acetyloxygalactoside represented by the following formula, and then subjecting the product to debenzylation or detriethylsilylation reaction

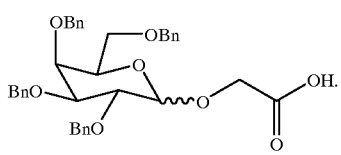

23. A method for producing the taxoid derivative of claim 13, comprising after protecting a hydroxyl group at the 7-position of 10-deacetyl-baccatin III with chlorotriethylsilane, reacting the product with tetrabenzyl acetyloxymannoside represented by the following formula, and then subjecting the product to debenzylation or detriethylsilylation reaction

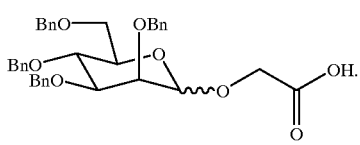

24. A method for producing the taxoid derivative of claim 10, comprising reacting 10-deacetyl-baccatin III with tetrabenzyl acetyloxygalactoside represented by the following formula, and then subjecting the product to debenzylation reaction

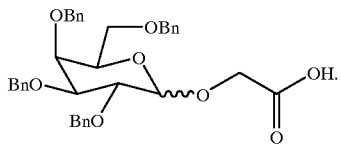

25. A method for producing the taxoid derivative of claim 11, comprising reacting 10-deacetyl-baccatin III with tetrabenzyl acetyloxymannoside represented by the following formula, and then subjecting the product to debenzylation reaction

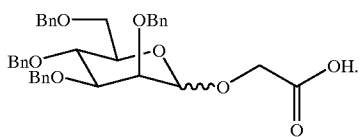

26. An antitumor agent comprising galactosyloxyacetyl-10-docetaxel as an active ingredient

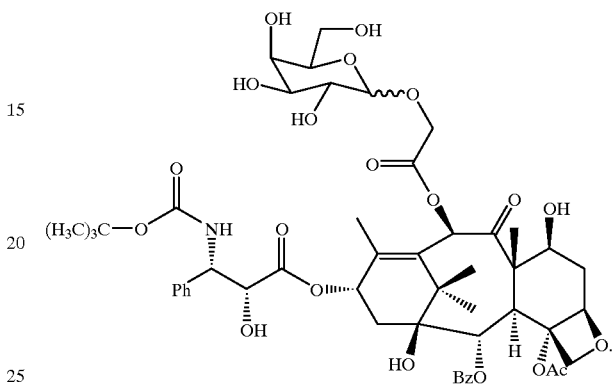

27. An antitumor agent comprising mannosyloxyacetyl-10-docetaxel as an active ingredient

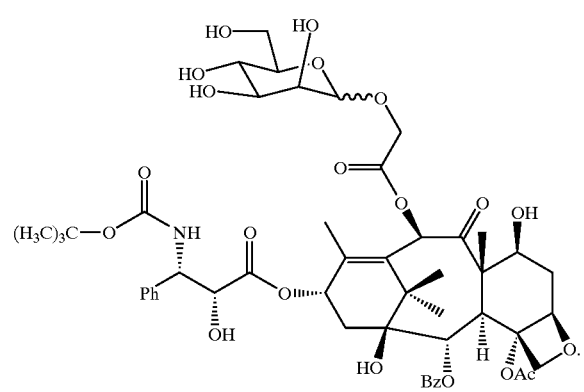

* * * * *